(12) United States Patent
Pugia et al.

(10) Patent No.: US 8,263,414 B2
(45) Date of Patent: Sep. 11, 2012

(54) DISPENSING OF A DIAGNOSTIC LIQUID ONTO A DIAGNOSTIC REAGENT

(75) Inventors: Michael J. Pugia, Granger, IN (US);
James A. Profitt, Goshen, IN (US);
Lloyd S. Schulman, Osceola, IN (US);
Chris T. Zimmerle, Goshen, IN (US);
Hai-Hang Kuo, Granger, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1099 days.

(21) Appl. No.: 11/135,928

(22) Filed: May 23, 2005

(65) Prior Publication Data

US 2006/0263902 A1     Nov. 23, 2006

(51) Int. Cl.
*G01N 1/10* (2006.01)
(52) U.S. Cl. ........ 436/180; 422/500; 422/501; 422/502; 422/503; 347/51
(58) Field of Classification Search ............ 422/99–102, 422/500–503; 347/51; 436/180
See application file for complete search history.

(56) References Cited

U.S. PATENT DOCUMENTS

| | | | |
|---|---|---|---|
| 4,502,054 A * | 2/1985 | Brescia et al. ................. 347/55 |
| 5,063,396 A | 11/1991 | Shiokawa et al. ......... 346/140 R |
| 5,084,397 A | 1/1992 | Siddons et al. ............... 436/518 |
| 5,110,555 A | 5/1992 | Moore et al. .................. 422/100 |
| 5,408,535 A | 4/1995 | Howard, III et al. ............. 382/1 |
| D359,357 S | 6/1995 | Bigler et al. ................. D24/186 |
| 5,437,840 A * | 8/1995 | King et al. .................. 422/82.08 |
| 5,449,898 A | 9/1995 | Dosmann .................... 250/208.1 |
| 5,518,179 A | 5/1996 | Humberstone et al. .... 239/102.2 |
| 5,654,803 A | 8/1997 | Howard, III et al. ......... 356/446 |
| 5,677,195 A | 10/1997 | Winkler et al. ............... 436/518 |
| 5,701,181 A | 12/1997 | Boiarski et al. ............... 356/446 |
| 5,763,262 A | 6/1998 | Wong et al. ................. 435/287.2 |
| 5,807,522 A * | 9/1998 | Brown et al. .................... 422/50 |
| 5,877,863 A | 3/1999 | Ross et al. ..................... 356/445 |
| 6,121,048 A * | 9/2000 | Zaffaroni et al. ............... 506/14 |
| 6,180,417 B1 | 1/2001 | Hajizadeh et al. ............. 436/518 |
| 6,270,214 B1 | 8/2001 | Smith et al. ................... 347/101 |
| 6,394,363 B1 | 5/2002 | Arnott et al. ................ 239/102.1 |

(Continued)

FOREIGN PATENT DOCUMENTS

EP        841 164 A1     5/1998

(Continued)

OTHER PUBLICATIONS

Journal of Clinical Laboratory Analysis 9:212-217 (1995); Evaluation of an Automated Urine Chemistry Reagent-Strip Analyzer; J. Lott, William R. Johnson, and Karl E. Luke.

(Continued)

*Primary Examiner* — Jyoti Nagpaul
(74) *Attorney, Agent, or Firm* — Noam R. Pollack

(57) ABSTRACT

Biological fluid samples are deposited by methods that produce a uniform layer of the sample over a reagent-containing surface. In one embodiment, a nozzle having multiple openings is used to deposit a sample over the reagent-containing surface simultaneously. In an alternative embodiment, single droplets of the sample are deposited in a pattern on the surface, preferably in a sequence of parallel lines. The reaction between the biological sample and the reagents is read from a spectrographic image of the reagent-containing surface obtained by optical methods.

10 Claims, 4 Drawing Sheets

U.S. PATENT DOCUMENTS

| | | | |
|---|---|---|---|
| 6,565,197 B1 | 5/2003 | Murray et al. | 347/85 |
| 6,602,719 B1 | 8/2003 | Carpenter | 436/518 |
| 6,656,432 B1 | 12/2003 | Hirota et al. | 422/100 |
| 2004/0018613 A1 | 1/2004 | Shoji | |

FOREIGN PATENT DOCUMENTS

| | | |
|---|---|---|
| EP | 1 088 863 A1 | 4/2001 |
| EP | 1 094 119 A | 4/2001 |
| EP | 1 107 004 A2 | 6/2001 |
| EP | 1 107 004 A3 | 4/2003 |
| EP | 1 324 038 A2 | 7/2003 |
| EP | 1 324 038 A3 | 4/2005 |
| JP | 2001186880 | 7/2001 |
| JP | 2001186881 | 7/2001 |
| JP | 2001337096 | 12/2001 |
| JP | 2001343386 | 12/2001 |
| JP | 2004045346 | 2/2004 |
| JP | 2005249436 | 9/2005 |
| WO | WO 2004/017376 A | 2/2004 |
| WO | 2004/036228 A1 | 4/2004 |

OTHER PUBLICATIONS

Clinical Biochemistry, vol. 29, No. 3. pp. 217-223 (1996), The Canadian Society of Clinical Chemists, Evaluation of the CLINITEK® ATLAS™ for Routine Macroscopic Urinalysis, Valerian C. Dias, Terry Moschopedis, Connie Prosser, and Randall W. Yatscoff.

Office Action of Japanese Patent Application No. 2008-513597 issued on May 31, 2011.

* cited by examiner

DISPENSING OF A DIAGNOSTIC LIQUID ONTO A DIAGNOSTIC REAGENT

FIELD OF THE INVENTION

This invention relates to reagents and instruments used to measure the quantity of analytes in biological samples by the reaction of the analytes with reagents to produce an optical response.

BACKGROUND OF THE INVENTION

Many instruments have been developed to measure the quantity of analytes in various biological samples, for example urine, blood, salvia, or extracts of mucus or tissue. Typically, a sample liquid is applied to a surface containing reagents that react with the analyte. The reagents produce a detectable response that is measured and related to the amount of the analyte. The surface can be hydrophilic or hydrophobic in nature, e.g. filter paper compared to polystyrene. Some devices use combinations, such as urinalysis strip tests that use hydrophilic filter paper pads on top of a hydrophobic polystyrene handle. In the typical test, a strip containing reagents is dipped, i.e. fully immersed in a liquid sample, and the reaction between the analyte in the sample and the reagents is measured, typically by optical methods. Other devices include microchips that use hydrophilic substrates connected to capillaries molded of polystyrene. The reagents themselves can be water soluble or insoluble and dried onto the supporting surface, as in test strips. Or, they could be added as a liquid to a microchip. Additional liquid reagents can be applied to the surfaces already containing dried reagents. Typically this application occurs after a sample has been applied. The sample volume should be as small as possible for obvious reasons relating to cost and convenience. What is less obvious is that it is often difficult to obtain uniform and accurate responses when applying small amounts of liquid reagents or biological samples to surfaces containing reagents.

Most biological samples and liquid reagents will have a significant water content and thus will be compatible with hydrophilic substrates and incompatible with hydrophobic surfaces. The samples and reagent liquids when dispensed spread rapidly across hydrophilic substrates and are repelled by hydrophobic substrates. The contact between the dispensed liquid and the reagents on the surface can be made by capillary action or directly. However, when substrates are relatively hydrophobic, the dispensed liquid will form beads on the surface of the substrate that attempt to minimize their contact with the surface. Dispensed liquids therefore do not spread uniformly over the reagent. Another difficulty associated with dispensing liquids is that the dried reagents may be either water soluble or water insoluble in nature. The insoluble dry reagents may not be readily accessible to the liquid samples, or soluble reagents may be dissolved and move with the liquid on the substrate. The reagents ideally should contact the sample uniformly since the measurable response of the reagents to the sample, e.g. color development, should be uniform in order to obtain an accurate reading of the analyte in the sample.

Another problem related to obtaining good contact between a dispensed liquid and a reagent on a surface is related to the physical nature of the samples. They vary in their physical properties such as surface tension, viscosity, total solids content, particle size and adhesion. Therefore they are not easily deposited in consistent volumes uniformly over the reagent-covered substrate. Also, as the amount of the liquid sample is reduced, it becomes increasingly difficult to apply a consistent amount of a sample with varying properties to the reagents. In contrast, ink-jet printing and the like rely on liquids developed for such uses and having consistent physical properties.

Deposition of droplets of liquid is a familiar operation. Examples include the ink jet-printer, either piezoelectric or bubble actuated, which forms print from the controlled deposition of multiple small droplets of about 2 to 300 μm diameter (typically 50 μm) containing from a few femtoliters to tens of nanoliters. Other methods of depositing small droplets have been proposed, which generally employ piezoelectric principles to create droplets, although they differ from typical ink-jet printers. Examples are found in U.S. Pat. Nos. 5,063,396; 5,518,179; 6,394,363; and 6,656,432. Deposition of droplets of larger droplets through syringe type pipette is known to be reproducible in diagnostic systems from 3 to 100 μL. This corresponds to single droplet diameters of about 2 to 6 mm. A commercial example of such pipette systems is the CLINITEK ALTAS® urinalysis analyzer. The droplet size can be greater or less than the nozzle size depending on the nozzle shape, pump type and pressures applied.

The problems discussed above are particularly observed when a liquid sample is dispensed as droplets onto a reagent-containing pad. The applicants found that the interactions of the pad's surface and the reagents were creating inaccurate responses when the sample was added as a droplet, rather than completely covering the reagent pad by immersing the reagent pad (dipping it) into the sample liquid, as is frequently done. Large droplets on the order of 3 to 100 μL do not transfer into the reagent when the substrate is too hydrophobic and form a bubble on the surface. They overwhelm the reagent with excess fluid if the surface is hydrophilic. Smaller droplets, of a few femtoliters to tens of nanoliters, can also be a problem when deposited on a substrate that is too hydrophobic as they lack the volume to completely cover the surface area and will randomly aggregate in non-uniform patterns. Small drops also allow open spaces for migration of water-soluble reagents. These tiny droplets are also prone to evaporation of liquids and to formation of aerosols, which are considered to be bio hazardous if comprised of urine or blood specimens. Thus, if a liquid is to be deposited as droplets on test pads, rather than dipping the pads in the sample, improvements are needed.

After contact between dispensed liquids and reagents is complete, the results may be read using one of several methods. Optical methods are commonly used, which rely on spectroscopic signals to produce responses. Results must be reproducible to be useful. Optical measurements are affected by the reagent area viewed and by the time allowed for the dispensed liquids and reagents to react. Formation of non-uniform areas within the field of view and changes in the amount of reaction time needed increase errors. For example, a measurement made of a sample or reagent which has spread non-uniformly across the substrate gives a different result each time it is read.

It is always an objective of those who develop and improve methods of analyzing biological samples to provide accurate and consistent results. The present inventors propose new methods for improvement in the results obtained when liquid biological samples or liquid reagents are deposited on surfaces containing dried reagents, particularly when the sample is deposited as droplets.

SUMMARY OF THE INVENTION

The invention includes methods of depositing biological fluids and liquid reagents ("liquids") uniformly onto surfaces having an area containing reagents ("reagent area") that react with an analyte in the biological fluids and apparatus for carrying out such methods. The optical response resulting from the reaction of the analytes in biological fluids with the reagents is viewed as a spectroscopic image that can be examined in pre-defined regions of the image.

A biological fluid or liquid reagent is dispensed using a nozzle positioned close to the reagent-containing surface, e.g. 1-5 mm from the surface. The liquid is dispensed as droplets having an average diameter of about 0.1 to 2.0 mm (100 to 2000 μm) and an average volume ranging from microliters to nanoliters. The reagent area, or an area adjacent to the reagent area, is covered with dispensed liquid and the resulting reaction is read by optical methods within a predetermined region of the reagent-containing area as a function of the time needed for the reaction of the dispensed liquid with the reagent-containing surface. The entire reagent-containing surface maybe covered at one time, or alternatively it may be covered in a predetermined pattern of droplets in a sequence that reacts uniformly with the reagent.

In one embodiment, multiple openings in a nozzle dispenses multiple droplets simultaneously to cover a predetermined region of the reagent area (see FIG. 1). Each opening in the nozzle has a diameter of about 0.1 to 1.0 mm and is capable of producing droplets of about 50% to 200% of the diameter of the opening. The nozzle openings are arrayed so as to cover a predetermined region area of the reagent area. Thus, nozzle openings are sufficient to cover the predetermined region on the surface either simultaneously or in multiple passes, which may be done by moving the droplet-dispensing nozzle or the reagent-containing surface, or both.

In a second embodiment, one opening in a nozzle dispenses droplets (see FIG. 2). The opening in the nozzle has a diameter of about 0.1 to 1.0 mm and is capable of producing droplets of about 50% to 200% of the diameter of the opening. A pattern may be formed by traversing the reagent-containing surface in a predetermined sequence of lines, e.g. about 1 to 100 passes across the reagent surface, by moving the droplet-dispensing nozzle or the reagent-containing surface, or both.

In a third embodiment, the biological fluid or liquid reagent is dispensed by either single or multiple hole nozzles onto the surface adjacent to the reagent area such that the droplets are uniformly transferred into the reagent-containing area by capillary action (see FIG. 3). The dispense pattern may be formed by traversing the surface in a sequence of lines, e.g. about 1 to 100 passes across the reagent surface.

In other embodiments, a liquid reagent (or reagents) are applied to the reagent area, either before, after, or with the deposition of the biological sample. Preferably, the liquid reagent is applied after the biological sample has been dispensed.

Exposing the reagent-containing area to a light of a suitable wavelength provides information on the reaction that occurs between the analyte in the biological sample and the reagents in the form of a spectrographic image that is read in predetermined regions of the image to more accurately measure the amount of the analyte in the biological sample. The predetermined regions may be the entire reagent-containing area, portions thereof, or the area covered by a singled droplet.

DESCRIPTION OF THE PREFERRED EMBODIMENTS

Definitions

Figure 1:
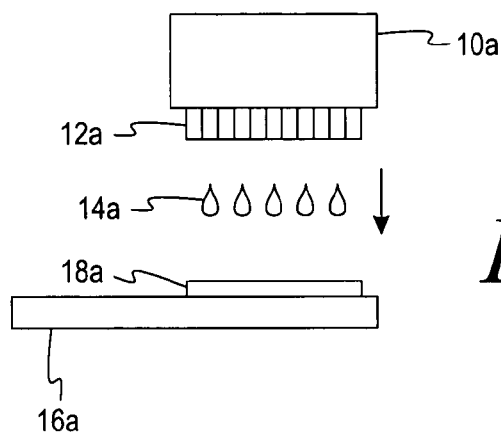
FIG. 1 shows a sectional view of a multiple hole nozzle dispensing liquid droplets in a first embodiment of the invention.

The following terms used herein are defined as follows:

"Spectrographic image" refers to a detailed view of the optical response of a reagent-containing area to a biological sample deposited on the reagent-containing area, which enables examination of sub-units of the entire reagent-containing area.

"Hydrophilic" surfaces are those that have a less than 90° contact angle between the surface and a drop of water placed thereon.

"Hydrophobic" surfaces are those that have a 90° or larger contact angle between the surface and a drop of water placed thereon.

"Figure of Merit (FOM)" is a calculated measure of performance in which the mean difference between results obtained from samples with and without an analyte present is divided by the square root of the sum of the squares of standard deviations, the results comparing samples without the analyte and samples containing the lowest analyte concentration that can be detected.

The objective achieved by the methods of the invention is to cover a reagent-containing surface with a uniform layer of a liquid to obtain improved accuracy of results. Each portion of dispensed liquid contacts the reagent-containing surface and makes direct contact to a corresponding portion of the reagents, so that the reaction of the analyte in each portion of the sample occurs where the liquid was deposited. As will be seen in the discussion that follows, typical reagent-containing surfaces may not be well suited for dispensing of droplets because of their hydrophobic or hydrophilic properties relative to the biological sample with which they are to react.

Dipping a reagent-containing surface in a liquid sample achieves complete and uniform contact with the reagents. The present invention accomplishes similar results without the need for immersing the reagent-containing surface and provides several advantages. First, by dispensing droplets, rather than dipping the reagent-containing surface, less sample is needed and the amount of dry and liquid reagents required is generally reduced. Second, manual steps such as adding liquid reagents by hand, can be eliminated. Also, automated analysis, in which small test areas are placed on a card or strip, becomes easier to implement. Either the card or strip or the nozzle can be moved to permit multiple tests of a single sample liquid or a single test of multiple samples. This results in being able to dispense on demand to reagent areas of interest.

Of particular importance to the invention is the improved accuracy and precision (repeatability) that can be obtained over standard pipette systems. The improved accuracy and precision results from being able to read the results of the response of the reagents to the sample by viewing a focused spectroscopic image across the entire reagent area as a function of time and position. A particular benefit of the small drop sizes used in the invention (in the range of 0.1 to 1 mm diameters) is that they are readily absorbed by very hydrophobic surfaces, while large drop sizes are not. An additional advantage of the small drop sizes is that patterns can be dispensed that allow using reagents-containing cards without carry-over between adjacent reagent areas.

Effect of Reagents on Liquid Absorbed

A series of tests was carried out to demonstrate the impact of dispensing on accuracy and precision of the measurements made of the reaction of a biological sample with reagents.

Reagents from the MULTISTIX® products (Bayer) were tested with CHEKSTIX liquids (Bayer) or other standardized test solutions containing and lacking analytes to be detected. Some of the reagent surfaces were hydrophobic while others were hydrophilic. Some of the reagents tested were water-soluble while others were water-insoluble (see Table 1). In all cases the reagents contained on a porous pad of bibulous (i.e. absorbent) material placed on top of a non-porous polystyrene film as a substrate.

In a first test, the typical performance of reagents was established by dipping (immersing) a fixed area (5×5 mm) of the reagent-containing pad into an aqueous test sample. The maximum volume of liquid absorbed by the reagent surface after dipping was determined by the change in weight of the fixed area. In a second test, a pipette was used to dispense this same maximum volume as large droplet sizes (1.7 to 20.4 µL) onto the reagent surface. The performance of reagents after dispensing the large droplet sizes was measured by a CLINITEK STATUS® urinalysis strip reader and compared to the performance when dipped (see Table 2). In a third test, a micropump with a single nozzle was used to dispense a series of small droplets sizes (100 nL to 1 uL) onto the reagent surface (FIG. 1). Again, the performance of reagents after dispensing the small droplet sizes was measured and compared to the performance after dipping (see Table 2).

The performance of reagents was measured as a Figure-of-Merit (FOM) using the response to a series of test samples that either lacked or contained the analyte being measured. Figure-of-Merit (FOM) was calculated as the absolute difference between the mean results for two test samples lacking and containing a low concentration of the analyte divided by the square root of the sum of the squares of standard deviations observed at each level. Higher values of FOM are preferred, but for the present tests, a value of at least 7-10 indicates acceptable performance. Figure-of-Merit (FOM) values were calculated for dipped reagents and for reagents that had the sample liquids dispensed as large and ideal droplet sizes (see Tables 1 and 2).

TABLE 1

The performance of reagent surfaces after dipping in test liquids.

| Reagent for | Volume of sample (µL) | Surface energy of reagent pads | Water solubility of reagents | FOM |
|---|---|---|---|---|
| Urobilinogen | 7.4 | Hydrophilic | Insoluble | 10.1 |
| Occult blood | 7.4 | Hydrophilic | Insoluble | 15.3 |
| pH | 7.4 | Hydrophilic | Insoluble | 21.0 |
| Protein | 8.3 | Hydrophilic | Soluble | 38.0 |
| Creatinine | 6.5 | Hydrophilic | Soluble | 13.9 |
| Bilirubin | 14.1 | Hydrophilic | Soluble | 28.1 |
| Specific gravity | 9.5 | Hydrophilic | Insoluble | 13.5 |
| Nitrite | 20.4 | Hydrophilic | Very soluble | 19.9 |
| Leukocyte | 17.0 | Hydrophilic | Very soluble | 12.1 |
| Ketone | 6.5 | Hydrophilic | Very soluble | 11.3 |
| Albumin | 8.3 | Hydrophobic | Insoluble | 13.0 |
| Glucose | 1.7 | Very Hydrophobic | Insoluble | 19.2 |
| Polystyrene without reagent | 0.2 | Very Hydrophobic | NA | NA |

Pipetting Droplets Compared to Dipping

It was evident that reagent-containing pads absorbed varying amounts of liquid when dipped depending on the composition (Table 1). In general, very hydrophobic reagent surfaces absorbed less liquid. The very hydrophobic polystyrene surface having a surface tension of 70 dynes/cm² held a film of only 0.2 µL. A significant variation in the amount of liquid picked up was found among dry reagents of similar surface energy and affected by the reagent ingredients.

Figure 4:
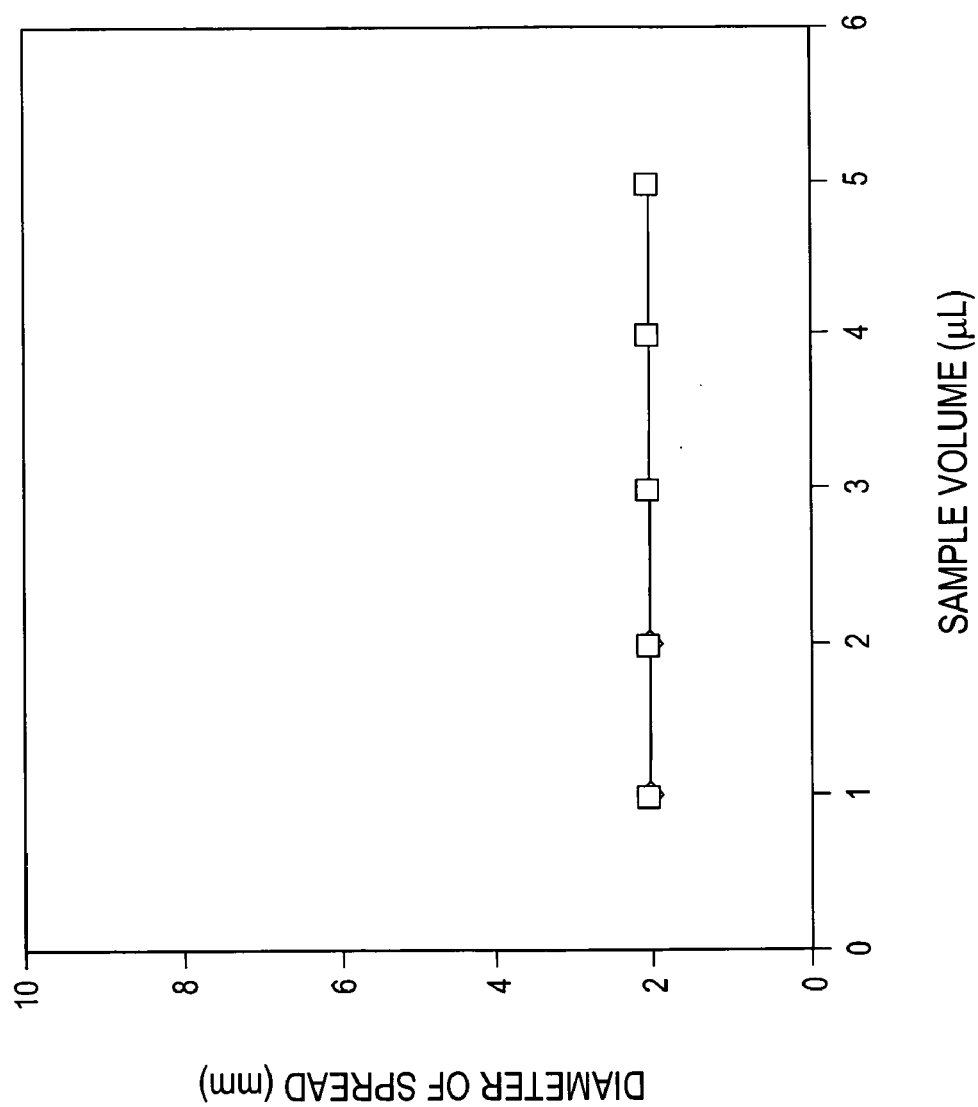
FIG. 4 shows the spread area of dispensed liquid on a highly hydrophobic reagent surface.

In additional tests using a pipette to dispense relatively large droplets of samples (1.7 to 20.4 µL) did not provide as uniform response from the reagents as desirable (see Table 2). The FOM values for large droplets were lower than FOM values for dipping. FOM values are smaller when the difference between the results with and without an analyte in the sample is small and the standard deviation is large. Therefore, accuracy and consistency of the measurements of the analyte in a sample liquid were worse when large droplets were used. There are several reasons for the poor performance. Large droplets could not give a response for the very hydrophobic reagents (e.g. glucose) as the droplets did not enter the porous pad and make contact with the dry reagent. Droplets formed a ball on the surface of the reagent and did not spread (See FIG. 4 in which the diameter of the drop did not increase as liquid was added). Another reason was that large droplets applied to reagents with water soluble liquids (e.g leukocyte) have poor response compared to dipping because the reagent migrates as the drop spreads across the surface. The large droplets produce excess liquid on the porous pad by overwhelming the water absorbing capacity, resulting in migration. This also increases the probability that carry-over contamination will occur between dry reagent areas that should receive separate liquid samples. A final reason for poor performance of large droplets was observed in hydrophobic surfaces with water insoluble reagents (albumin). In this case poor absorption of the dispensed liquids generates uneven applications and non-uniform signals.

Figure 5:
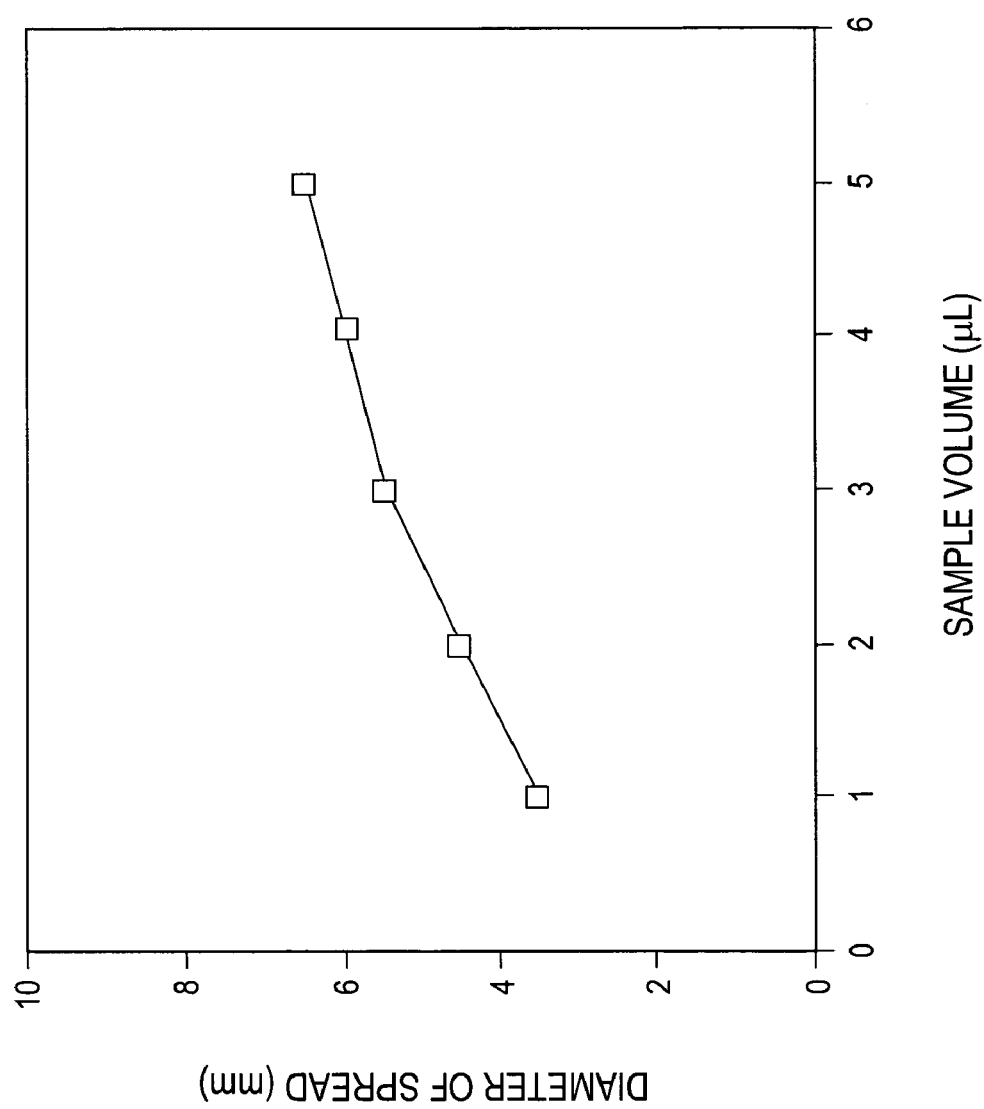
FIG. 5 shows the spread area of dispensed liquid on a highly hydrophilic reagent surface.

Generally, droplets were applied to the middle of each pad. The liquid coverage observed depended on the droplet size (see FIG. 5 in contrast with FIG. 4) and the total volume applied. It was found that the amount to fill the reagent pad with liquid by pipette was often less than that found by dipping. Generally, about 6-8 µL of total liquid volume was needed to reach agreement performance between pipetting and immersion in the test solution. It was concluded that achieving equivalent performance when depositing sample liquids in droplets, compared with dipping, required precise deposition of the sample. Ideal liquid volumes dispensed by droplets were selected based on the best FOM achieved (Table 2). When small droplets were deposited, multiple drops were used to achieve the ideal total volume. It was concluded that, depending on the properties of the test pad, the volume of liquid deposited as droplets should be varied to assure equivalent performance. When this was done the FOM achieved with small droplet sizes equaled or surpassed the performance of dipping for all reagent surface types (compare Table 1 and 2).

TABLE 2

The performance of reagent surfaces after depositing droplets of test liquids.

| | Large droplets sizes (1.7 uL to 20.4 uL) | | Small droplets sizes (100 nL to 1 uL) | |
|---|---|---|---|---|
| Reagent for | Observation | FOM | Observation absorption | FOM |
| Urobilinogen | Absorbed | 9.8 | Absorbed | 11.2 |
| Occult blood | Absorbed | 14.9 | Absorbed | 17.3 |
| pH | Absorbed | 22.0 | Absorbed | 36.5 |
| Protein | Overly absorbed | 3.5 | Absorbed | 41.2 |
| Creatinine | Overly absorbed | 8.4 | Absorbed | 14.1 |
| Bilirubin | Overly absorbed | 3.4 | Absorbed | 27.6 |

TABLE 2-continued

The performance of reagent surfaces after depositing droplets of test liquids.

| Reagent for | Large droplets sizes (1.7 uL to 20.4 uL) Observation | FOM | Small droplets sizes (100 nL to 1 uL) Observation absorption | FOM |
|---|---|---|---|---|
| Specific gravity | Absorbed | 9.6 | Absorbed | 13.3 |
| Nitrite | Overly absorbed | 6.1 | Absorbed | 22.3 |
| Leukocyte | Overly absorbed | 2.3 | Absorbed | 15.3 |
| Ketone | Overly absorbed | 8.4 | Absorbed | 12.1 |
| Albumin | Poorly absorbed | 6.3 | Absorbed | 10.6 |
| Glucose | Not absorbed | 0.1 | Absorbed | 10.6 |

Effect of Volume and Drop Size and Dispense Pattern

In addition to the need to correlate the performance of results obtained when pipetting sample liquid onto a reagent pad with the volume of liquid, it is also important to determine how the volume deposited affects the spreading of liquid. A study was undertaken to evaluate the effect of increasing the amount of liquid droplets on the spread of the liquid on a hydrophilic surface and a very hydrophobic reagent surface. It was found that as the droplet size was increased, the diameter of the liquid on the hydrophilic reagent pad increased (see FIG. 5), as might be expected. But, in the case of a very hydrophobic reagent pad (Glucose) little absorption and expansion of the liquid occurred when large droplets were used (see FIG. 4). However, it was surprising to find that when the droplet size was under 100 nL, the liquid was instantaneously absorbed and expansion occurred (relative to the size of the droplet). That is, when the droplets are small, the hydrophobic reagent pad behaves as if it is hydrophilic. It was concluded that deposition of multiple smaller droplets would be preferred to provide uniform coverage. Also, by controlling of the sample volume, more efficient use of the available reagent pad should be possible.

Problem of Hydrophobic Surfaces

When a reagent pad is very hydrophobic, for example the glucose pad used in these tests, it is difficult for the liquid sample to penetrate the pad with large droplets. (Note the results of the tests on liquid absorption in FIG. 4). In the glucose pad, this may be done intentionally to limit the entry of the sample liquid. The color change from the reaction of glucose in the sample with the reagents only occurs where the liquid touches the surface under the base of a drop sitting on the surface. Therefore, it would be preferred to deposit many small droplets over a defined area in order to obtain the best results, rather than to pipette large droplets. When this is done the performance equal to or greater than that of dipping can be achieved (Note the FOM achieved with small droplets in Table 2).

Depositing Onto Reagent-Containing Areas

FIG. 1 illustrates a first embodiment of the invention, in which a nozzle 12a is supplied from liquid chamber 10a and multiple nozzle openings dispense droplets 14a onto a reagent-containing area 18a, which is supported on a hydrophobic surface 16a.

Figure 2:
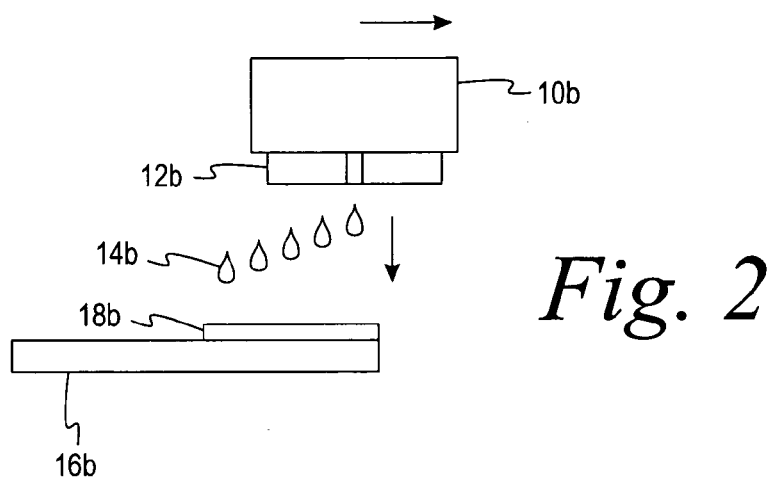
FIG. 2 shows a sectional view of a moving nozzle dispensing liquid droplets in a second embodiment of the invention.

FIG. 2 illustrate a second embodiment of the invention, in which a nozzle 12b is supplied from liquid chamber 10b and a single nozzle opening dispenses droplets 14b onto a reagent-containing area 18b, which is supported on a hydrophobic surface 16b. In this embodiment the nozzle is moved or the reagent-containing area is moved relative to the nozzle to deposit droplets in a predetermined pattern.

A liquid can also be dispensed onto a very hydrophobic substrate, for example a portion of a polystyrene substrate that is offset from the reagent area. This is a third embodiment of the invention, illustrated in FIG. 3. A liquid chamber 10c supplies nozzles 12c that dispense droplets 14c to the hydrophobic surface 16c adjacent to a reagent-containing area 18c. The liquid sample will migrate to the reagent containing area via capillary action. Capillary action can be achieved either by capillaries in the polystyrene leading the fluid to the reagent or by capillaries in the reagent area wicking the liquid in. With large droplets, liquid contact is poor. Droplets larger then the capillaries, either in the reagent or in the polystyrene, do not transfer into the reagents; the droplets instead form a bubble.

In two test cases, one large droplet of 4 uL and 40 small droplets of 0.1 uL were applied to polystyrene off-set from the glucose reagent area. In a first case, test droplets were placed in contact with a micro capillary of 150 by 100 microns by 4 mm long that was in contact with the glucose reagent area. The large droplet was not transported through the capillary in 60 seconds while the smaller droplets moved through the capillary and into the reagents with in a few seconds. Therefore a response was measurable only with the small droplets. In a second case, test droplets were placed in contact with the capillaries inside glucose pad. The large droplets were reluctant to migrate into the pad in less than 60 seconds. As the pad contained many capillaries some migration occurred. The smaller droplets readily entered the pad. The FOM determined for the large droplet case was <3, while the FOM for the small droplet case was 22.1, demonstrating the performance advantage for small droplet application. Similarly improved results were obtained for small droplets when the glucose reagent was replaced with affinity membranes containing immunoassay reagents for detecting hCG, hbA1c and Uristatin.

Problem of Water Soluble Reagents

When water-soluble reagents are in the reagent surface, the sample liquid, e.g. urine, absorbs them. Then, as the liquid spreads on the reagent area, the water-soluble ingredients move with the liquid at the solvent front. This migration creates a non-uniform color development. Tests with water-soluble ingredients were used to measure migration. The leukocyte reagent (containing water-soluble ingredients) tested with large drops indicated substantially the same results, regardless of the sample volume and whether the sample contained leukocytes or not (FOM of <3, Table 2). However, when the test pads were dipped in the sample liquid or the liquid was applied in small droplets, the presence or absence of leukocytes was readily determined (FOM of >10, Tables 1 or 2). Spreading of water soluble ingredients was apparent in either dipping or small droplet application. Simultaneous coverage of the reagent surface with repeated application of small droplets limited the migration and made any migration that occurred a predictable pattern. In the case of large droplets, (>3 uL) random aggregation caused non-uniformity in the migration. In the case of very small droplets (<10 nl), random aggregation also occurred along with evaporation. This created not only non-uniform migration but also open spaces lacking deposited liquid.

In one possible application, since spreading of the liquid is limited by the droplet volumes and spraying patterns onto the reagents areas, multiple test areas can be defined on a continuous surface of reagent (e.g. a long ribbon of reagent or a card of polystyrene containing such a ribbon) that is fed under the dispensing nozzle. The hole spacing could be adjusted to allow sufficient separation between individual reagent areas without liquid communication between the discrete reaction areas. The hole spacing also could be adjusted to provide a uniform response from the reagents and to avoid migration of water soluble reagents. In test cases, it was shown that droplets of 1 uL and less can be separated on a 5 mm by 6 in ribbon of reagent by properly spacing dispense patterns. The results were read by an optical read head positioned to direct light over the test area and to receive reflected light at a predetermined time after the sample liquid has been sprayed on the test area.

Properly Spacing Dispense Patterns

Figure 3:
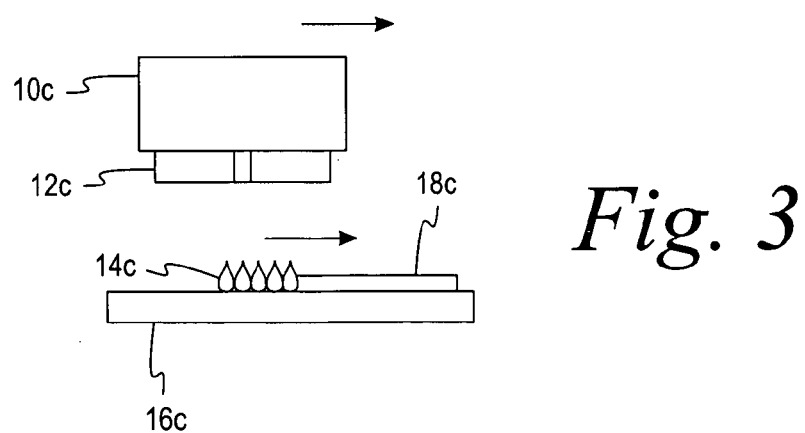
FIG. 3 shows a sectional view of a nozzle and a liquid in the third embodiment of the invention.

In a typical embodiment, the nozzle will be spaced about 5 mm or less above the reagent surface. In FIG. 1 to 3 the nozzle plate has been drilled with holes so that the droplets fall vertically onto the test area. The plate may also be curved with the droplets falling at an angle. To minimize cross contamination the distance between the nozzle and the test area will be as small as possible, typically greater than 1 mm and less than 5 mm for accurate droplet placement, as determined by the size of the droplets and their trajectory.

As demonstrated with ribbons, precisely depositing liquid makes it possible to space test areas closely on a substrate containing reagents, while avoiding cross-contamination. The number and size of the nozzle openings will vary depending on the application, but holes should be greater than 100 µm diameter, to avoid creating an aerosol. Since the nozzles will be sized to dispense droplets over a given size test area, it will normally be the case that the nozzle will be roughly the size of the test area as a minimum or much smaller when using multiple holes or multiple passes over the test area. The test area of course will be small, say about 1 to 25 mm square, and have any desired shape, although squares or circles are most common. Since the nozzles of the invention provide accurate placement of the sample liquid, the test areas can be closely spaced, thus improving efficiency and accuracy of the analysis. Depending on the water solubility of reagents, it was observed that the test areas could be spaced as close as about 1.3 to 10 mm (from center to center) with only about 0.3 to 8 mm between adjacent edges.

Relationship of Droplet Pattern to Optical Image

Figure 6:
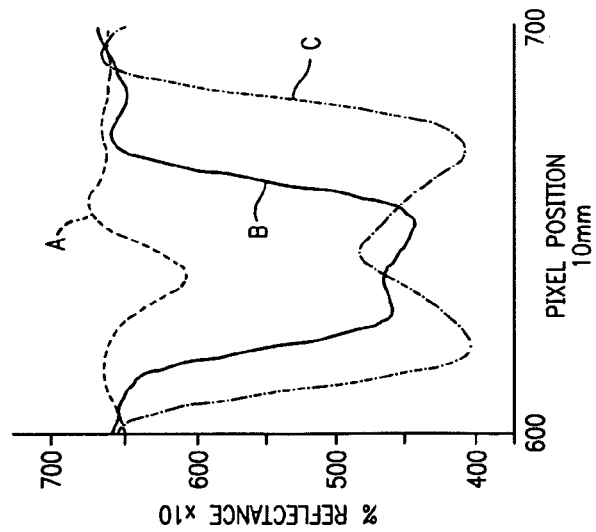
FIG. 6 shows the optical scan of a dispensed liquid as a function of time and drop size.
Figure 6A:
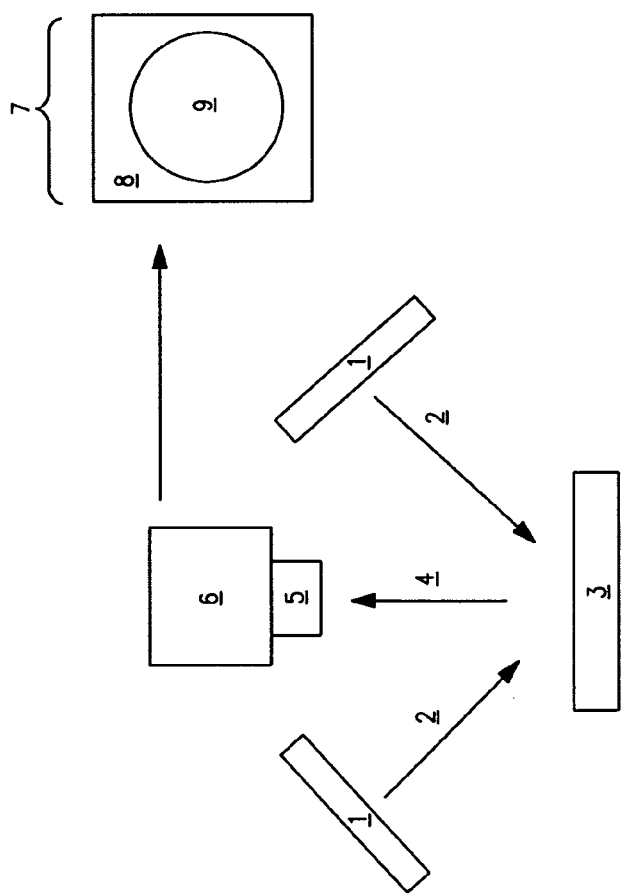

When this method of dispensing a small droplets onto a reagent area is adopted, it is possible to improve the method of reading the optical response to the reagents to the sample. In the conventional technology, the response of the reagents e.g. color development, is determined for the entire reagent area by supplying light having the desired wavelengths to the area and measuring the returned or transmitted light to a photo detector. The amount of light measured is correlated with the amount of the analyte in the sample that has reacted. In effect, an average of the color developed over the reagent area is read. A more accurate measurement would luminate the reagent area in a pattern and manner corresponding to the deposition of the sample liquid. That is, a light beam could traverse (scan) the reaction area and the returned or transmitted light could be received and measured, one spot (pixel) at a time. Such a process could be thought of as being analogous to the pattern traced on the screen of a cathode ray tube in a conventional television set. This is illustrated in FIG. 6a, in which light from light source 1 is directed (2) to a reagent surface 3. Reflected light 4 passes through a lens 5 and is detected by camera 6. The spectrographic image 7 is reported as shown in FIG. 6. Area 9 shows the region in which the reflectance is high while area 8 shows the region where reflectance is low.

As a result, a scanned spectrographic image can be obtained at predetermined times to provide spectral information at various pixel positions across the reagent surface. FIG. 6 shows the spectrographic image across a reagent surface in the x-direction. In FIG. 6, ten pixels equals 1 mm, so the width being examined is 10 mm. The results could be averaged across the selected scan area and reported as the total color developed, which would then be related to the analyte present in the reagent area. The scanned image was found to be dependent on time and drop size. The larger droplet size ("C") (8 µL or 2.5 mm diameter) formed even more uneven patterns when the reagents contained water soluble ingredients due to migration at the solvent front as previously mentioned, resulting in lower reflectance at the outer edges of the droplets. The smaller droplet size ("A and B") (20 droplets of 0.5 µm diameter) formed even more patterns with the same reagent, provided enough time was allowed for reagents to react. Curve A shows the droplets soon after being dispensed; Curve B shows the spread at a later time. This method of reading the optical response of the reagents is particularly well suited to the dispensing of individual droplets in traces that cover the area, but it could also be used with the embodiment of the invention in which a spray nozzle is used, as described above.

Lower Limit of Droplet Size

The droplet size limit of 100 nL was chosen to accommodate urine as a sample liquid, which includes particulates (e.g. cell, casts, crystal, bio-molecules and the like) that affect the ability of the nozzle holes less than 100 um to deliver consistent size droplets. It was further shown that hole diameters greater than 100 µm allow sufficient separation to flush out particulates and to prevent carry-over cross contamination. Since the total sample liquid will be equivalent to that delivered as a single droplet by a pipette, about 1 to 1000 small droplets are delivered over a short period, say about 0.2 to 5 seconds, the nozzle hole is used repeatedly and must not clog. The desired result was that hole diameters greater than 100 µm allowed thousands of small droplets are deposited uniformly over the reaction area to provide a uniform response from the reagents. Additional problem observed with hole diameters smaller than 100 µm were evaporation of liquid before absorption was completed and the formation of aerosols.

More generally, it is believed that droplets of less than 100 µm diameter could be used when the fluid is a liquid reagent without particles and the dispense height is close to the reagent surface.

Nozzle Arrays

The nozzles may be supplied with sample fluid or reagent under pressure from a source, which may be for instance, a syringe pump, diaphragm pump, pressurized container, piezo actuator, diaphragm, peristaltic, vortex, suction, centrifugal and the like with or without check-valves, splitters, air supply and venting Many arrangements are contemplated within the scope of the invention. It is expected that the nozzles will be used in automated analyzers where advantage can be taken of their superior coverage of the test area. For example, more than one nozzle could be used, arranged in groups of 1 to 20, supplied by 1 to 20 liquid sources, either individually or in groups. The nozzles could be supplied and replaced individually or in groups. Since the nozzles may require replacement after depositing 100 to 1000 samples, either for cleaning or for disposal, they would be likely made in groups that are easily removed and replaced.

In another embodiment, the entire reagent area is not covered simultaneously with sample liquid by deposition from a nozzle containing many openings. Instead, the reagent area is covered with small droplets, one at a time, tracing out patterns in the reagent area. This process is analogous to the ink jet printer in that droplets are deposited in lines, but rather than forming characters separated by spaces free of ink, the present process covers substantially all of the reagent area and assures that all of the reagents react with the sample and as uniformly as possible. Depositing droplets in this matter requires movement of the depositing nozzle (or nozzles) or the reagent area, or both. Preferably, the reagent area is moved under a stationary dispensing nozzle (or nozzles).

In a typical reagent area of about 25 mm² a series of traces could be deposited beginning at one edge and proceeding in parallel traces until the opposing edge is reached. The width of each trace may vary depending on the size of the droplets and the spreading of each droplet after it lands on the reagent area. For example, with droplets having a diameter of 100 to 1000 μm, the reagent area of 25 mm² would be covered with about 50 to 5 linear traces, for a total of about 2500 to 25 droplets. The process would be carried out in only about 0.01 to 2 seconds. Other patterns could be used to cover the entire reaction area, such as a circular trace beginning at the center of the area and moving outward in a spiral until the outer edge of the area is reached.

In two embodiments, the present invention includes the substitution of a nozzle with one or more small holes (FIGS. 1 & 2) having diameters of about 100 to 1000 μm. Since individual dry reagent areas that are typically used for analysis are small, say about 1 to 25 mm square, the nozzle includes enough openings cover a measurable amount of the reagent surface with small droplets in as few passes as possible. As these small droplets require nozzle holes of about 100 to 1000 μm in diameter, the number of holes may range from 1 to 10 for every mm² surface to be covered by the nozzle.

In addition to using single nozzles, other possible arrangements include multiple nozzles, each one supplied from one or more containers for the liquids to be dispensed. The nozzle or nozzles could be moved from one test area to another, or the test areas could be moved under stationary nozzles. In one arrangement, multiple nozzles are used to dispense different liquid samples onto reagents. For example, to be useful in the Clintek Atlas®, an automated urine analyzer (Bayer Corporation), a nozzle must be arrayed to dispense over 40 separate urine samples onto at least 12 reagents. The nozzle container also must be washable between samples. Alternatively, an array of nozzles with separate containers could be used, with each dispensing a separate sample or with each dispensing the same sample onto separate test areas.

Adding Reagents

In more conventional technique reagents are added to a bibulous surface e.g. an absorbent pad, and then dried. The biological fluid sample is added and after sufficient time has elapsed for color or other optical response to develop, the reagent-containing surface is read and correlated with the amount of an analyte in the sample. In the present invention the precise deposition of the biological sample and the spectroscopic imaging of the reagent area makes it possible to deposit additional reagents as desired at the time the biological sample is being tested.

In one embodiment of the invention, after the biological sample has been deposited on the reagent area, an additional reagent (or reagents) is deposited on all or selected portions of the reagent area.

Alternatively, or additional reagent (or reagents) could be deposited before the biological sample is placed on the reagent area. This could serve to activate other reagents already in place, for example, or to add a reagent having a short shelf life that could otherwise not be used.

In still another embodiment, the additional reagent (or reagents) could be added simultaneously with the biological sample. This method could provide mixing needed for lysis of cells, affinity reactions, chemical reaction and dilutions.

Depositing Liquid Reagent After the Sample

A liquid can be dispensed onto a reagent area after the sample has been added. For example, 3 μL of urine was added to the glucose reagent followed by 3 μL of phosphate buffer pH 6.5. The urine sample made liquid contact with the reagent at 0 seconds and the color reaction is started. The liquid buffer makes liquid contact with the reagent 10 seconds later and the color reaction continues. The FOM is reduced when high specific gravity urine is used as the sample as the glucose reagent result is inhibited by high chloride content in the sample. With application of a secondary liquid reagent after the sample, variations between the low and high sample are reduced and the FOM is improved due to the lowered dissolved salt in the diluted sample, as shown in Table 3.

TABLE 3

The performance of glucose reagent surfaces after dispensing sample followed by test liquids.

|  | Small droplets sizes without secondary liquid reagent | | Small droplets sizes with secondary liquid reagent | |
| --- | --- | --- | --- | --- |
| Glucose sample | Observation absorption | FOM | Observation absorption | FOM |
| low SG urine | Absorbed | 10.6 | Absorbed | 12.2 |
| high SG urine | Absorbed | 5.4 | Absorbed | 11.3 |

What is claimed is:

1. An apparatus for dispensing a uniform layer of droplets from a sample of a biological fluid from at least 1 mm above a surface containing reagents for reacting with said reagents comprising:
   (a) a nozzle for dispensing said sample of a biological fluid, said nozzle having a closed channel ending in one or more openings having diameters greater than 100 μm and up to about 1000 μm for dispensing under pressure said sample of biological fluid as droplets having diameters in the range of 0.1 to 2 mm onto a predetermined region of said reagent-containing surface;
   (b) a reservoir for supplying said biological sample to said nozzle of (a);
   (c) automated means for positioning said nozzle with respect to said reagent-containing surface or said surface with respect to said nozzle such that said nozzle is positioned at least 1 mm above said reagent-containing surface during dispense such that the droplets fall onto the reagent-containing surface;
   (c) means for dispensing under pressure said biological sample via said nozzle openings onto predetermined portions of said reagent-containing surface; and
   (d) means for reading the results of the reaction between said biological fluid and said reagents from a spectrographic image of the reagent-containing surface.

2. An apparatus of claim 1, wherein said predetermined region of said surface is the entire reagent-containing region.

3. An apparatus of claim 1, wherein said predetermined region of said surface is the area contacted by one droplet dispensed by said nozzle openings.

4. An apparatus of claim 1, wherein said predetermined region of said surface is a portion of said surface containing reagents.

5. An apparatus of claim 1, wherein said means for reading the results of the reaction between said biological fluid and said reagents includes a source of light directed onto a predetermined portion of said spectroscopic image and a detector for measuring the light returned from said portion of said spectroscopic image.

6. An apparatus of claim 1, wherein said predetermined region of said spectroscopic image consists of the entire reagent-containing surface.

7. An apparatus of claim 1, wherein said predetermined region of said spectroscopic image consists of the area contacted by one droplet.

8. An apparatus of claim 1, wherein said predetermined region of said spectroscopic image consists of a portion of said reagent-containing surface.

9. An apparatus of claim 1 further comprising means for dispensing reagent liquids onto said reagent-containing surface through the one or more openings in said nozzle.

10. An Apparatus of claim 1 wherein said nozzle dispenses droplets under pressure when said nozzle is positioned from 1 to 5 mm above said reagent-containing surface.

* * * * *

UNITED STATES PATENT AND TRADEMARK OFFICE
CERTIFICATE OF CORRECTION

PATENT NO.      : 8,263,414 B2                           Page 1 of 1
APPLICATION NO. : 11/135928
DATED           : September 11, 2012
INVENTOR(S)     : Michael J. Pugia et al.

It is certified that error appears in the above-identified patent and that said Letters Patent is hereby corrected as shown below:

In the Claims:

1) In Claim 5, Column 13, line 4, please delete "spectroscopic" and insert --spectrographic--.
2) In Claim 5, Column 13, line 6, please delete "spectroscopic" and insert --spectrographic--.
3) In Claim 6, Column 13, line 8, please delete "spectroscopic" and insert --spectrographic--.
4) In Claim 7, Column 13, line 11, please delete "spectroscopic" and insert --spectrographic--.
5) In Claim 8, Column 14, line 2, please delete "spectroscopic" and insert --spectrographic--.

Signed and Sealed this
Ninth Day of July, 2013

Teresa Stanek Rea
*Acting Director of the United States Patent and Trademark Office*